United States Patent [19]

Gager

[11] 4,173,072

[45] Nov. 6, 1979

[54] DENTAL CROWN REMOVER

[75] Inventor: John C. Gager, Alexandria, Va.

[73] Assignees: Terry W. Gager; Terry W. Gager; Francine Oster, all of Alexandria, Va.

[21] Appl. No.: 777,713

[22] Filed: Mar. 15, 1977

[51] Int. Cl.² .............................................. A61C 3/16
[52] U.S. Cl. ...................................... 433/120; 29/252
[58] Field of Search ......................... 32/43; 254/93 R; 29/261

[56] References Cited

U.S. PATENT DOCUMENTS

| | | | |
|---|---|---|---|
| 403,293 | 5/1889 | Rosenthal | 32/43 |
| 1,109,096 | 9/1914 | West | 32/43 |
| 1,666,860 | 4/1928 | Maranda | 32/43 |
| 2,490,284 | 12/1949 | Simart | 254/93 R |
| 3,069,761 | 12/1962 | Sommer | 254/93 R |
| 3,653,127 | 4/1972 | Ballard | 32/43 |
| 3,690,006 | 9/1972 | Lozano et al. | 32/43 |

FOREIGN PATENT DOCUMENTS 296568  4/1971  U.S.S.R. ....................................... 32/43

*Primary Examiner*—Russell R. Kinsey
*Assistant Examiner*—John J. Wilson

[57] ABSTRACT

A dental crown or bridge remover comprising crown or bridge gripping means, and a power actuated linear ram attached thereto, having a drive means arranged to permit gentle and gradual dislodgement or separation of the crown or bridge from the underlying tooth system without causing damage.

3 Claims, 9 Drawing Figures

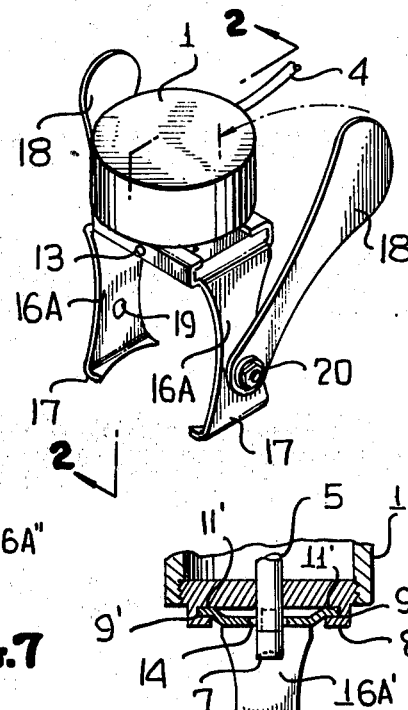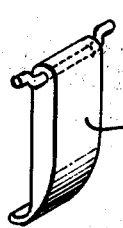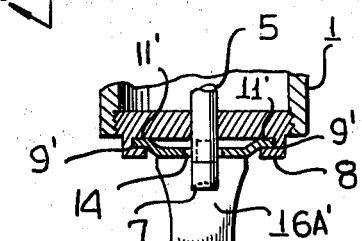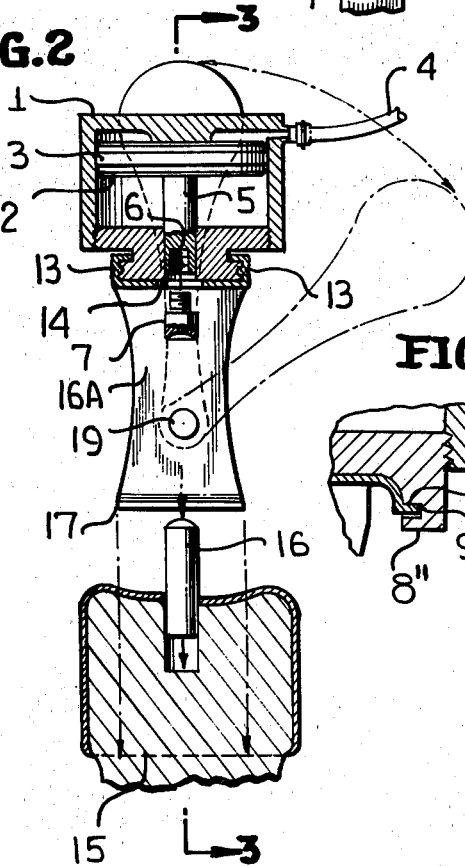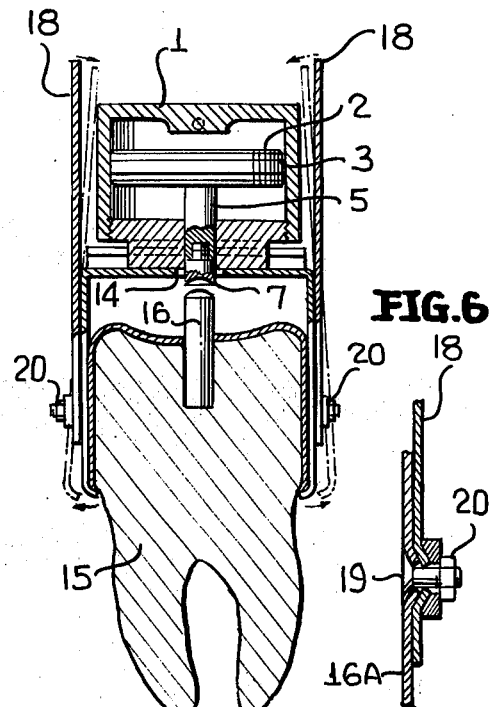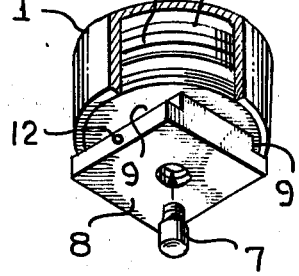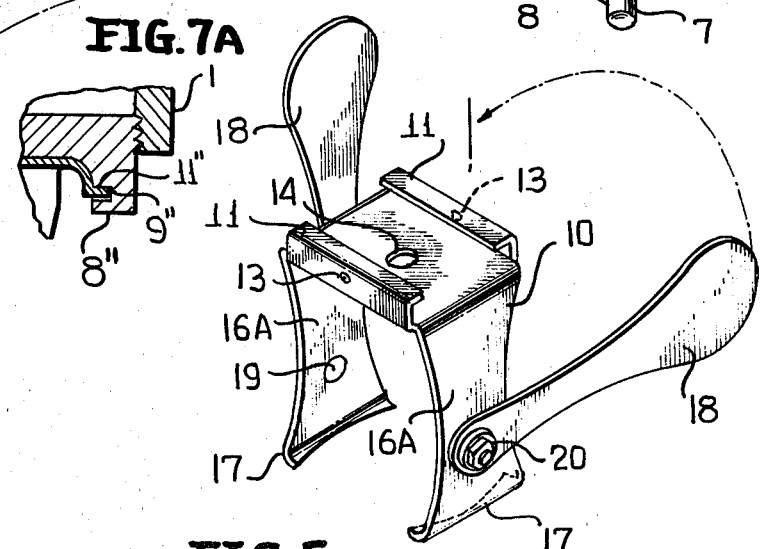

4,173,072

DENTAL CROWN REMOVER

BACKGROUND OF THE INVENTION

The prior art is replete with devices intended to accomplish the desired result. Most of the prior art devices rely upon the mechanical advantage obtained from a rotatable screw thread to effect the dislodgement, separation, or removal; illustrative of this is the U.S. Pat. No. 403,293, issued to C. H. Rosenthal on May 14, 1889. Devices of this character require considerable mechanical dexterity as well as strength, and it is evident from the references, that often lever sticks and the like were necessarily introduced into the mouth in order to apply the necessary force, and this inevitably introduces considerable twisting moments of inertia, and other strains difficult to control, all of which is not conducive to the patient's or the operator's comfort and ease of mind. The recent U.S. Pat. to Louis M. Ballard, No. 3,653,127, issued Apr. 4, 1972, takes a step in the direction of applying the principle of fluid power to the solution of the related problems encountered, in a particular way. It is broadly the object of the present invention to couple the advanced state of the art of miniature fluid actuated devices wherein problems of zero leakage, compatible materials and temperature ranges, smoothness and reliability of operation, lend to providing a novel means to perform in a practical way, the operation of removing dental crowns or bridges

DETAILED DESCRIPTION OF THE INVENTION

It is an object of the present invention to provide an improved dental tool for taking a crown or bridge off of the underlying tooth system, quickly and gently and without causing trauma or apprehensiveness in the patient, and without causing damage to any of the parts involved.

It is a further object of the invention to employ with maximum efficiency the use of fluid power transfer so that only the necessary force, and that directed in only the desired direction is developed for accomplishing the removal in a clean, dry, and safe manner.

It is a further object of the invention to provide such a dental tool which is simple, compact, and easy to attach to the crown or bridge, and is easily operated without great force or dexterity on the part of the operator.

It is yet a further object of the invention to provide a dental tool of this character which is capable of being used at all tooth positions in the mouth without awkwardness or difficulty.

The aforementioned objects, as well as others of the invention, will become more readily apparent on reading the further description in conjunction with the drawings in which:

FIG. 1 is a perspective view of the invention in one form.

FIG. 2 is a cross-section view on line 2—2 of FIG. 1, an exploded view showing the arrangement of parts and their manner of attachment to a crown on underlying tooth structure.

FIG. 3 is a cross-section view on line 3—3 of FIG. 2 suggesting the manner of using the invention, and with the piston partially moved outwardly, but no separation of the crown having yet taken place.

FIG. 4 is a perspective view of the bottom of the fluid actuated cylinder, including one type of detachable attaching means.

FIG. 5 is a perspective view of a type of lifting clamp.

FIG. 6 is an enlarged fragmentary detail of hole 19, and the means of fastening a pinching member 18 to an arm 16-A.

FIG. 7 is a cross-section view of a modified overall heighth reducing manner of attaching the lifting clamp to the cylinder.

FIG. 7-A is a further modification, providing for greater strength and heighth reduction at the critical points.

FIG. 8 is a modified form of lifting jaw.

It will be apparent from the drawing of the various forms of the invention that there has been provided modest but useful improvement to either the clamp shown in the aforementioned patent issued to Charles Henry Rosenthal, or the pair of jaws which serve a like purpose in the U.S. Pat. No. 3,690,006 issued on Sept. 12, 1972 to Gustavo Jiminez Lozano, et al, of Buenos Aires, Argentina, in that a miniature fluid, or other power actuated cylinder is coupled to the lifting means, in lieu of the usual hand powered types of actuating means disclosed in the prior art. This is made possible because in the present state of the art, it is possible to manufacture, economically, a satisfactory power actuated means, particularly a fluid power cylinder device, or an electrically operated type device, which will provide a practical solution to a long evident problem encountered by the practicing dentist. The drawing and description will be confined to the teaching of a fluid power actuating means, but it will be understood that other means could provide the same effect, including, but not limited to an electrically operated device of appropriate size and strength.

Looking now at the drawing, and more particularly at FIG. 1, a pancaked miniature fluid actuated cylinder 1 of rudimentary design, having a conventional piston 2 of thin design, and with a seal 3 of usual type, making up the well known expansible chamber, with an inlet 4 capable of admitting fluid under pressure so as to expand the volume of the chamber by driving piston 2 outwardly, and therewith piston rod 5 attached thereto, said piston rod having its outer end internally threaded as shown at 6 to receive mating male threads which may for example be part of a tool-piece 7, which when attached firmly to the end of the piston rod, should be so dimensioned that in the retracted position, its face will be substantially flush with the outer surface of nose-piece 8 rigidly attached to the lower end of the cylinder. The nose-piece 8 is provided with a pair of parallel grooves 9 which form a track structure element that permits, under appropriate conditions, the detachable attachment of lifting clamp 10 by means of its cooperating flanges 11 which have symmetrically located dimples 12 capable of engaging similar and corresponding dimplesor depressions located on the nose-piece 8 and marked 13 on the drawing, all for the purpose of providing a snap-lock feature for correctly locating the clamp as it is slid into place, so that piston rod 5 wih tool-piece 7 screwed in, will be ale to pass through hole 14 in the lifting clamp 10 when the piston is actuated by application of fluid pressure to inlet 4. The outer end of tool-piece 7 is made concave so that it may loosely capture the convex end of a driving pin 16 which is inserted in the conventional drilled hole in a crown, such as the one best shown in FIG. 5 of the aforementioned Rosenthal patent, and carried along in our drawing as well, this still being present standard practice in most instances. The lifting clamp 10 has a pair of arms 16-A, and they should be fashioned of a material like spring steel so as to have a degree of resilience such as to make possible the easy attachment of the lifting clamp 10 to a range of shell crown sizes which may be encountered. Each arm has at its extremity a flange 17 which will engage the crown in the manner shown in Rosenthal's patent, and also indicated in the drawings here, however in the present invention there is provided a hole 19 in each of the arms 16-A near the flange 17 for the purpose of attaching a pinching member 18 by means of fastening elements 20, all as best shown in FIG. 6, so that the pinching member may be rotated as desired about the resulting axis pinching member 18 can be grasped between the thumb and a finger when appropriately positioned, to accomplish opening of arms 16-A as shown in phantom in FIG. 3 for application to to a crown or the like. The countersunk hole, flat-head bolt, cooperating washer, and nut are arranged so that there will be no unwanted interference, and so that the degree of frictional resistance can be regulated so that the pinching member can be easily managed. It should be understood that in practice it may be necessary to have a somewhat larger diameter cylinder than that depicted in the drawing, in order to obtain the needed force, however this does not create an insurmountable obstacle since the rotatable feature provides the necessary accomodation.

A method of using the invention as it has been thus far described will be set forth, which is suitable for all tooth locations in the mouth, with the understanding that with proficiency, short cuts will become obvious. Also the embodiment thus far described will undoubtedly require more than one size of clamp to accomodate all contingencies, and the full range of tooth sizes, furthermore, an assortment of driving pins in varying lengths and diameters should be kept on hand, or means for cutting them from stock as needed, provided. To perform the operation the lifting clamp as shown in FIG. 5 of the accompanying drawing will be manipulated for attachment to the crown, using the pinching members previously described in the most helpful manner, and thereafter moving them to a non-interfering position. When the clamping operation has been completed, a short measuring stick or wire is used to determine the depth of the pre-drilled hole in the crown by bottoming it in the hole and determining the distance to the upper surface of hole 14, an appropriately sized driving pin is selected, and placed in position thru hole 14, and thereafter the cylinder is slid into place until the dimples or depressions previously described have performed their function. The inlet 4 must be oriented towards the center of the mouth so that a fluid supply hose may be fairly led out of the mouth to a source of fluid pressure. The fluid pressure is gradually applied and the operation is effortlessly, smoothly, gently, and without any traumatic effect, accomplished.

Several modifications that are illustrated in the drawing, and their merits will now be detailed. It is desirable to keep the overall heighth to a minimum, and this may be accomplished by modifying the nose-piece and clamp assembly flanges as shown in FIG. 7, or FIG. 7-A that is the supporting pin member which is part of the modified free swinging type claw or jaw member 16-A" shown in FIG 8 may be arranged to cooperate with the modified structure 8' and 9' as illustrated in FIG. 7, so that a pair of claw members of the type illustrated in FIG. 8 may be substituted for the one piece clamping type member as best shown in FIG. 5. A further modification can be made to accomodate the claw or jaw member in the supporting structure 8" and 9" shown in FIG. 7-A, in this case the protrusions of the pin member of the free swinging jaw or claw 16" are made without any offset and instead are perfectly straight so as to provide the desired cooperative support. The structure shown in FIG. 7 is relatively easy to assemble and disassemble, but somewhat sacrifices maximum heighth reduction, and strength or resistance to the forces of separation which may be encountered in use. On the other hand the modification shown in FIG. 7-A maximizes heighth reduction and resistance to the forces encountered which tend to cause separation, however closer attention must be paid to the proceedure of assembly and diassembly. The modified parts are marked correspondingly in the Figures with prime numerals, and double prime numerals.

FIG. 8 shows a modification using jaw pieces like those shown in the U.S. Pat. No. 3,690,006 previously mentioned herein, and hereby incorporated by reference. Depending upon the arrangement of the nose-piece 8 prime or double prime, the pins of the jaw member shown in FIG. 8, may be straight or offset, alternatively, the nose-piece may be designed so that either or both jaw members may be permanently pivotally attached so as to be non-slideable, and in the manner shown in the aforementioned Lozano Patent; the whole object being to obtain maximum economy of manufacture, flexibility in use, and the ability to eliminate the separate driving pin 16 and tool-piece 7 and use instead a screwed-in driving pin which is assembled after assembling cylinder, appropriate lifting structure and screwed-in driving pin outside of the mouth, in contradistinction from the first described mode of use.

Having described the invention in some of the numerous possible forms and recognizing the possibility of devising a miniature electric screw jack which would be the mechanical equivalent of the fluid actuated cylinder, and further arranging details of the lifting structure so as to lift orthodontic bands and the like, the breadth of the invention will be limited only by the scope of the appended claims:

I claim:

1. A dental crown or bridgework remover comprising crown or bridgework gripping means having attached thereto a power actuated ram including drive means arranged to drive in the direction of the biting surface of the associated crown or bridgework in a direction generally normal thereto so as to separate said crown or bridgework from its underlying tooth system.

2. The invention of claim 1 wherein the drive means enters a pre-drilled hole in the crown or bridgework and drives against the underlying tooth system to effect separation.

3. The invention of claim 1 wherein the gripping means is detachable from the power actuated means.

* * * * *